United States Patent
Lu et al.

(10) Patent No.: US 12,221,409 B2
(45) Date of Patent: Feb. 11, 2025

(54) METHOD FOR PREPARING CHIRAL ALKYL COMPOUNDS BY ASYMMETRIC HYDROGENATION OF OLEFINS CATALYZED BY IRON COMPLEX

(71) Applicant: Zhejiang University, Zhejiang (CN)

(72) Inventors: Zhan Lu, Zhejiang (CN); Peng Lu, Zhejiang (CN); Xiang Ren, Zhejiang (CN)

(73) Assignee: Zhejiang University, Hangzhou (CN)

(*) Notice: Subject to any disclaimer, the term of this patent is extended or adjusted under 35 U.S.C. 154(b) by 19 days.

(21) Appl. No.: 18/210,771

(22) Filed: Jun. 16, 2023

(65) Prior Publication Data

US 2024/0174588 A1    May 30, 2024

Related U.S. Application Data

(63) Continuation of application No. PCT/CN2021/130103, filed on Nov. 11, 2021.

(30) Foreign Application Priority Data

Jan. 22, 2021   (CN) .......................... 202110092710.1

(51) Int. Cl.
```
C07C 41/20      (2006.01)
B01J 31/12      (2006.01)
C07B 35/02      (2006.01)
C07B 53/00      (2006.01)
C07C 5/03       (2006.01)
C07C 17/354     (2006.01)
C07C 37/055     (2006.01)
C07D 209/08     (2006.01)
C07D 317/22     (2006.01)
C07D 317/50     (2006.01)
B01J 31/22      (2006.01)
C07F 15/02      (2006.01)
```
(52) U.S. Cl.
CPC ............ *C07C 41/20* (2013.01); *B01J 31/12* (2013.01); *C07B 35/02* (2013.01); *C07B 53/00* (2013.01); *C07C 5/03* (2013.01); *C07C 17/354* (2013.01); *C07C 37/055* (2013.01); *C07D 209/08* (2013.01); *C07D 317/22* (2013.01); *C07D 317/50* (2013.01); *B01J 31/2217* (2013.01); *C07C 2531/22* (2013.01); *C07C 2602/12* (2017.05); *C07C 2602/42* (2017.05); *C07F 15/025* (2013.01)

(58) Field of Classification Search
USPC ........................................................ 568/579
See application file for complete search history.

(56) References Cited

U.S. PATENT DOCUMENTS

2012/0016092 A1   1/2012  Nagy et al.

FOREIGN PATENT DOCUMENTS

| CN | 104478919 A | 4/2015 |
|---|---|---|
| CN | 105461508 A | 4/2016 |
| CN | 108440591 A | 8/2018 |
| CN | 109503645 A | 3/2019 |
| CN | 110655456 A | 1/2020 |

OTHER PUBLICATIONS

Casnati et al. ("Recent Advances in Asymmetric Iron Catalysis", Molecules, Aug. 2020, 25, 3889, pp. 1-29) (Year: 2020).*
Connon et al. ("Further Developments and Applications of Oxazoline-Containing Ligands in Asymmetric Catalysis", Chemical Reviews, 121, May 21, 2021, pp. 6373-6521) (Year: 2021).*
Notice of Allowance of counterpart Chinese Patent Application No. 202110092710.1 issued on Mar. 1, 2022.
First Office Action of counterpart Chinese Patent Application No. 202110092710.1 issued on Sep. 28, 2021.
William S. Knowles, Asymmetric Hydrogenations (Nobel Lecture), Angew. Chem. Int. Ed., 2002, pp. 1998-2007, The Nobel Foundation.
Ryoji Noyori, Asymmetric Catalysis: Science and Opportunities (Nobel Lecture), Angew. Chem. Int. Ed., 2002, pp. 2008-2022, The Nobel Foundation.
Stefan Kaiser et al., Iridium Catalysts with Bicyclic Pyridine-Phosphinite Ligands: Asymmetric Hydrogenation of Olefins and Furan Derivatives, Angew. Chem. Int. Ed., 2006, pp. 5194-5197.

(Continued)

*Primary Examiner* — Ana Z Muresan

(57) ABSTRACT

Provided in the present invention is a method for preparing chiral alkyl compounds by the asymmetric hydrogenation reaction of iron complex catalysts catalysing olefins: using the disubstituted olefin shown in formula I as a raw material, atmospheric hydrogen as a hydrogen source, FeX2-8-OIQ complex as a catalyst, and a silane compound and acetonitrile as cocatalysts, and reacting for 12-24 hours under the action of a reducing agent to prepare the chiral alkyl compound shown in formula II. The method of the present invention has mild reaction conditions, simple operation, and high atom economy. In addition, the reaction does not require the addition of any other toxic transition metal (such as ruthenium, rhodium, and palladium), and has great practical application value in the synthesis of drugs and materials. The conversion rate of the reaction is also good, generally reaching >99%, and the enantioselectivity is also high, generally 70-99%.

I

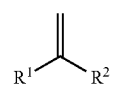

II

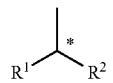

8 Claims, 1 Drawing Sheet

(56) References Cited

OTHER PUBLICATIONS

Mark J. Burk, Modular Phospholane Ligands in Asymmetric Catalysis, Acc. Chem. Res., Mar. 21, 2000, pp. 363-372, vol. 33, No. 6, American Chemical Society.

Maria Biosca et al., Asymmetric Hydrogenation of Disubstituted, Trisubstituted, and Tetrasubstituted Minimally Functionalized Olefins and Cyclic β-Enamides with Easily Accessible Ir-P,Oxazoline Catalysts, ACS Catal., Oct. 2, 2018, pp. 10316-10320, vol. 8, American Chemical Society.

R. Noyori et al., Asymmetric Synthesis of Isoquinoline Alkaloids by Homogeneous Catalysis, J. Am. Chem. Soc., 1986, pp. 7117-7119, American Chemical Society vol. 108, No. 22.

A. Miyashita et al., Synthesis of 2,2/-Bis(diphenylphosphino)-I,I/-binaphthyl (BINAP), an Atropisomeric Chiral Bis (triaryl) phosphine, and its use in the Rhodium(I)-Catalyzed Asymmetric Hydrogenation of a-(Acylamino)acrylic Acids, J. Am. Chem. Soc., 1980, pp. 7932-7934, American Chemical Society.

W. S. Knowles et al., Asymmetric Hydrogenation with a Complex of Rhodium and a Chiral Bisphosphine, Apr. 30, 1975, pp. 2567-2568, American Chemical Society.

Paivi Tolstoy et al., Iridium-Catalyzed Asymmetric Hydrogenation Yielding Chiral Diarylmethines with Weakly Coordinating or Noncoordinating Substituents, J. Am. Chem. Soc., Jun. 5, 2009, pp. 8855-8860, American Chemical Society.

Marc C. Perry et al., Optically Active Iridium Imidazol-2-ylidene-oxazoline Complexes: Preparation and Use in Asymmetric Hydrogenation of Arylalkenes, J. Am. Chem. Soc., 2003, pp. 113-123, American Chemical Society.

Peng Lu et al., Iron-Catalyzed Highly Enantioselective Hydrogenation of Alkenes, J. Am. Chem. Soc., Aug. 3, 2021, ppp. 12433-12438, American Chemical Society, vol. 143.

Jian-Hua Xie et al., Synthesis of Spiro Diphosphines and Their Application in Asymmetric Hydrogenation of Ketones, J. Am. Chem. Soc., 2003, pp. 4404-4405, vol. 125, No. 15, American Chemical Society.

Song Song et al., Enantioselective Iridium-Catalyzed Hydrogenation of β, γ-Unsaturated Carboxylic Acids: An Efficient Approach to Chiral 4-Alkyl-4-aryl Butanoic Acids, Angew. Chem. Int. Ed., 2012, pp. 2708-2711, vol. 51.

International Search Report of PCT Patent Application No. PCT/CN2021/130103 issued on Feb. 17, 2022.

Karolina Zukowska et al., Consequences of the electronic tuning of latent ruthenium based olefin metathesis catalysts on their reactivity, Beilstein Journal of Organic Chemistry, Aug. 20, 2015, pp. 1458-1468, vol. 11.

Paul J. Chirik, Iron- and Cobalt-Catalyzed Alkene Hydrogenation: Catalysis with Both Redox-Active and Strong Field Ligands, Accounts of chemical research, 2015, pp. 1687-1695, vol. 48, American Chemical Society.

Suzanne C. Bart et al., Preparation and Molecular and Electronic Structures of Iron(0) Dinitrogen and Silane Complexes and Their Application to Catalytic Hydrogenation and Hydrosilation, JACS Articles, Oct. 5, 2004, pp. 13794-13807, vol. 126, American Chemical Society.

Erin J. Daida et al., Considering FeII/IV Redox Processes as Mechanistically Relevant to the Catalytic Hydrogenation of Olefins by [PhBPiPr3]Fe-Hx Species, Inorganic Chemistry Article, Oct. 14, 2004, pp. 7474-7485, vol. 43, American Chemical Society.

Yusuke Sunada et al., Disilaruthena-and Ferracyclic Complexes Containing Isocyanide Ligands as Effective Catalysts for Hydrogenation of Unfunctionalized Sterically Hindered Alkenes, JACS Articles, Mar. 5, 2018, pp. 4119-4134, vol. 140, American Chemical Society.

Na Guo et al., Highly efficient and practical hydrogenation of olefins catalyzed by in situ generated iron complex catalysts, Organic Chemistry Frontiers, 2015, pp. 692-696, vol. 2.

Jianhui Chen et al., 10 gram-scale synthesis of a chiral oxazoline iminopyridine ligand and its applications, Organic Chemistry Frontiers, 2018, pp. 247-253, vol. 5.

Jordan M. Hoyt et al., Synthesis and Hydrogenation Activity of Iron Dialkyl Complexes with Chiral Bidentate Phosphines, Organometallics, Jun. 9, 2014, pp. 5781-5790, vol. 33, American Chemical Society.

Dominik J. Frank et al., Iron-catalysed alkene hydrogenation and reductive cross-coupling using a bench-stable iron (II) precatalyst, RSC Advances, 2013, pp. 25698-25701, vol. 3.

Jianhui Chen et al., Cobalt-Catalyzed Asymmetric Hydrogenation of 1,1-Diarylethenes, Organic Letters, Mar. 14, 2016, pp. 1594-1597, vol. 18, American Chemical Society.

* cited by examiner

METHOD FOR PREPARING CHIRAL ALKYL COMPOUNDS BY ASYMMETRIC HYDROGENATION OF OLEFINS CATALYZED BY IRON COMPLEX

CROSS-REFERENCE TO RELATED APPLICATIONS

The present application is a continuation application of PCT application No. PCT/CN2021/130103 filed on Nov. 11, 2021, which claims the benefit of Chinese Patent Application No. 202110092710.1 filed on Jan. 22, 2021. The contents of all of the aforementioned applications are incorporated by reference herein in their entirety.

TECHNICAL FIELD

The method refers to preparing chiral alkyl compounds by asymmetric hydrogenation of 1,1-disubstituted olefins catalyzed by an iminoquinoxazoline (8-OIQ) iron complex catalyst. In particular, this method could be used to prepare optically active chiral drug molecular intermediates.

BACKGROUND

Chirality is a basic attribute of nature. The "thalidomide event" has made people gradually realized the importance of chirality. Asymmetric hydrogenation of olefins is one of the most effective methods to obtain chiral compounds due to its atom-economy, simple operation, high activation and environmental-friendly. It has been widely used in the synthesis of chiral drugs, natural products, and industrial production of pesticide molecules. Knowles and Noyori won the Nobel Prize in Chemistry. [a) Knowles, W. S. *Angew. Chem. Int. Ed.* 2002, 41, 1998; b) Noyori, R. *Angew. Chem. Int. Ed.* 2002, 41, 2008.]

The core of the asymmetric hydrogenation of olefins is the design of metals and chiral ligands. The noble metals, such as rhodium, ruthenium and iridium play an dominant role in this field. The chiral ligands are mainly focus on bidentate phosphine containing ligands, such as DIPAMA, BINAP and Duphos. [a) Knowles, W. S.; Sabacaky, M. J.; et al. *J. Am. Chem. Soc.* 1975, 97, 2567; b) Miyashita, A.; Yasuda, A.; Takaya, A.; et al. *J. Am. Chem. Soc.* 1980, 102, 7932; c) Noyori, R.; Ohta, M., Hsiao, Y.; et al. *J. Am. Chem. Soc.* 1986, 108, 7117; d) Burk, M. J. *Acc. Chem. Res.* 2000, 33, 363; e) Xie, J. H.; Wang, L. X.; Fu, Y; et al. *J. Am. Chem. Soc.* 2003, 125, 4404; f) Tolstoy, P.; Engman, M.; Paptchikhine, A.; Bergquist, J.; Church, T. L.; Leung, A. W. -M.; Andersson, P. G.; *J. Am. Chem. Soc.* 2009, 131, 8855.; g) Kaiser, S.; Smidt, S. P.; Pfaltz, A. *Angew. Chem. Int. Ed.* 2006, 45, 5194.; h) Biosca, M.; Magre, M.; Pamies, O.; Diéguez, M.; *ACS Catal.* 2018, 8, 10316.; i) Perry, M. C.; Cui, X. H.; Powell, M. T.; Hou, D. -R.; Reibenspies, J. H.; Burgess, K. *J. Am. Chem. Soc.* 2003, 125, 113.]. However, the high cost, low earth abundance, and environmental impact associated with these noble elements inspires the search for catalysts with less toxic, more cost-effective, earth-abundant metals, such as Fe, and Co. Moreover, the potential unique features in 3d metal catalysis, such as a single-electron process, smaller d orbitals, multiple oxidation and spin states might provide new opportunities to solve the challenges of noble metal catalytic systems. Among them, iron is the second largest metal element in the earth's crust, and it has good biological compatibility. So far, the iron-catalyzed asymmetric hydrogenation of alkenes is not be realized. Therefore, it is very important to develop new ligands and iron catalysts for asymmetric hydrogenation of olefins. [a) Bart, S. C.; Lobkovsky, E.; Chirik, P. J. *J. Am. Chem. Soc.* 2004, 126, 13794-13807; b) Hoyt, J. M.; Shevlin, M.; Margulieux, G. W.; Krska, S. W.; Tudge, M. T.; Chirik, P. J. *Organometallics* 2014, 33, 5781-5790. c) Chirik, P. J. *Acc. Chem. Res.* 2015, 48, 1687. d) Guo, N.; Hu, M. -Y.; Feng, Y.; Zhu, S. -F. *Org. Chem. Front.*, 2015, 2, 692-696; e) Frank, D. J.; Guiet, L.; Käslin, A.; Murphy, E.; Thomas, S. P. *RSC Adv.* 2013, 3, 25698. f) E. J. Daida and J. C. Peters, *Inorg. Chem.*, 2004, 43, 7474. g) Sunada, Y; Ogushi, H.; Yamamoto, T.; Uto, S.; Sawano, M.; Tahara, A.; Tanaka, H.; Shiota, Y; Yoshizawa, K.; Nagashima, H. *J. Am. Chem. Soc.*, 2018, 140, 4119-4134.]. According to literature research, the iron-catalyzed asymmetric hydrogenation of olefins has the following challenges. First, iron has variable valence (−2 to +5), so it is challenging to design appropriate ligands to stabilize the metal valence of iron. Secondly, the iron is easy to dissociate with ligand after the catalyst was activated by activating reagent, which leads to the background reaction and get racemized product. [Hoyt, J. M.; Shevlin, M.; Margulieux, G. W.; Krska, S. W.; Tudge, M. T.; Chirik, P. J. *Organometallics* 2014, 33, 5781.]

In 2016, the Lu group developed an oxazoline iminopyridine (OIP) coordinated cobalt-catalyzed asymmetric hydrogenation of 1,1-disubstituted alkenes. [Chen, J. -H.; Chen, C. -H.; Ji, C. -L.; Lu, Z. *Org. Lett.* 2016, 18, 1594.]. Subsequently, the OIP coordinated iron catalyst was used to catalyze the asymmetric hydrogenation of 1,1-disubstituted olefins. Unfortunately, the product was obtained with low yield and enantiopure excess. Therefore, it is of great significance to develop new iron catalysts for asymmetric hydrogenation of simple olefins.

BRIEF SUMMARY

The invention includes the asymmetric hydrogenation of minimally functionalized 1,1-disubstituted alkenes using the oxazoline iminoquinoline ligand (8-OIQ) iron complex, A series of substrates with various functional groups could smoothly transfer to products with good conversion and enantioselectivity. In addition, the catalyst could hydrogenate the 1,1-disubstituted olefins sterically specifically and the hindered trisubstituted C=C double bond was maintained. Through this invention, we can also easily synthesize useful pharmaceutical molecular intermediates.

The invention is realized by the following technical program:

A method for preparing chiral alkyl compounds by asymmetric hydrogenation of olefins catalyzed by iron complex catalyst, the method is as follows: a disubstituted olefin shown in Formula I is used as a raw material, atmospheric hydrogen is used as hydrogen source, $FeX_2$-8-OIQ complex is used as catalyst, hydrosilane and acetonitrile are used as co catalysts, and a chiral alkyl compound shown in Formula II is prepared by reaction for 12-24 hours under the activation of a reducing agent;

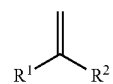

I

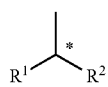

in Formula II, * represents a chiral carbon atom.

The reaction formula of the invention could be expressed as follows:

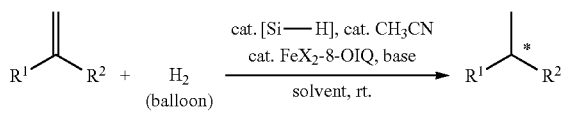

In Formula I or Formula II, $R^1$ is optionally selected from $C_2$~$C_8$ alkyl, naphthyl, a group shown in Formula III, or a N and O containing heterocyclic aryl group of $C_4$~$C_{10}$;

in $R^1$, the H on $C_2$~$C_8$ alkyl is not substituted or substituted by at least one substituent A, and the substituent A is phenyl, naphthyl, heterocyclic aryl or substituted phenyl; heterocyclic aryl is indolyl, pyridinyl, pyrrolyl, thiophenyl or furanyl; substituted phenyl is the phenyl group in which H on phenyl is replaced by at least one substituent B, and the substituent B is $C_1$~$C_3$ alkyl, $C_1$~$C_3$ alkoxy, halogen or $C_1$~$C_3$ alkylthio;

in $R^1$, the N and O containing heterocyclic aryl group of $C_4$~$C_{10}$ is pyridinyl, pyrrolyl, indolyl, benzodioxazolyl, benzoxazolyl or furanyl, preferably pyridinyl, indolyl or benzodioxazolyl;

in $R^1$, the H on naphthyl and the N and O containing heterocyclic aryl group of $C_4$~$C_{10}$ are not substituted or substituted by at least one substituent C, and the substituent C is $C_1$~$C_3$ alkyl or $C_1$~$C_3$ alkoxy;

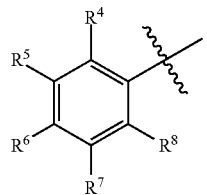

in $R^1$, among the groups shown in Formula III, $R^4$, $R^5$, $R^6$, $R^7$, $R^8$ are selected from any one of H, halogen, $C_1$~$C_2$ alkyl, $C_1$~$C_3$ alkoxy, benzyloxy, $C_1$~$C_3$ alkylthio, tert butyl dimethyl siloxy, trifluoromethyl, dimethylamino, pinacol borate, d-borneoxy, citronellol oxy, menthol oxy or geraniol oxy, and when $R^4$, $R^5$, $R^6$, $R^7$, $R^8$ are all H, Formula III is phenyl; and halogen is F or Cl.

In Formula I or Formula II, $R^2$ is optionally selected from $C_1$~$C_8$ alkyl, $C_2$~$C_8$ alkenyl, phenyl or benzyl; the H on $C_1$~$C_8$ alkyl and $C_2$~$C_8$ alkenyl are not substituted or substituted by at least one substituent D, which is phenyl, substituted phenyl, $C_1$~$C_3$ amino or 1,3-dioxolacyl.

Or in Formula I or Formula II, $R^1$ and $R^2$ are connected into a ring to form $C_9$~$C_{12}$ benzocycloalkyl; H on $C_9$~$C_{12}$ benzocycloalkyl is not substituted or substituted by at least one substituent E, wherein the substituent E is $C_1$~$C_3$ alkyl, $C_1$~$C_3$ alkoxy or halogen; preferably, $R^1$ and $R^2$ are linked to form benzocyclohexane.

$R^1$ and $R^2$ are different substituents.

Further, $R^1$ is preferably alkyl, naphthyl, 6-methoxynaphthalyl, pyridinyl, 2-methoxypyridyl, indolyl, N-methylindolyl, benzodioxazolyl or the group shown in Formula III.

In $R^1$, when $R^1$ is $C_2$~$C_8$ alkyl, H on $C_2$~$C_8$ alkyl is replaced by a substituent A. $R^1$ can be expressed as $R^A$—$(CH_2)_n$—, where n is an integer of 2 to 8. $R^A$ is a substituent A on the carbon chain, and $R^A$ is preferably phenyl, naphthyl or p-methoxyphenyl.

In $R^1$, the group shown in Formula III is preferably phenyl or substituted phenyl with 1-2 substituents, and the substituent on the substituted phenyl is preferably halogen, $C_1$~$C_2$ alkyl, $C_1$~$C_3$ alkoxy, benzyloxy, $C_1$~$C_3$ alkylthio, tent-butyl dimethyl siloxy, trifluoromethyl, dimethylamino, pinacol borate, d-borneol, citronellol-oxy, menthol-oxyl or geraniol-oxyl.

$R^2$ is preferably $C_2$~$C_6$ alkyl, $C_2$~$C_6$ alkenyl, phenyl or benzyl; H on $C_2$~$C_6$ alkyl is not substituted or substituted by substituent D, $R^2$ is the $C_2$~$C_6$ alkyl, and when H on the alkyl is substituted by substituent D, $R^2$ can be expressed as $R^D$—$(CH_2)_m$—, m is an integer of 2 to 6, and the substituent D is preferably phenyl, $C_1$~$C_3$ amino, 4-methoxyphenyl or 1,3-dioxolacyl.

In the invention, the silane compound is benzene silane ($PhSiH_3$) or n-octadecyl silane (n-$C_{18}H_{37}SiH_3$).

As a further improvement, an organic solvent is added to the method of this invention, and the organic solvent is any one of benzene, carbon tetrachloride, toluene, tetrahydrofuran, ether, dichloromethane, acetonitrile, dioxane, petroleum ether, cyclohexane, n-hexane, ethyl acetate, chloroform, and dimethylformamide, preferably toluene.

The amount of the organic solvent is generally 1-10 mL/mmol based on the amount of the disubstituted olefin shown in Formula I.

The reducing agent of the invention is any one of sodium triethylborohydride, sodium tri-sec-butyl-borohydride, lithium triethylborohydride, sodium tert-butoxide, potassium tert-butoxide, lithium tert-butoxide, sodium tert-pentoxide, sodium ethoxide, sodium methoxide and potassium methoxide, preferably is sodium triethylborohydride, sodium tert-butoxide, sodium ethoxide or sodium methoxide, more preferably is sodium triethylborohydride.

The invention takes the atmospheric hydrogen as the hydrogen source and inserts a hydrogen balloon on the reaction bottle.

As a further improvement, the mole ratio of the disubstituted olefin shown in Formula I, $FeX_2$-8-OIQ complex, silane compound, acetonitrile and reducing agent of the invention is 1:0.00001-0.1:0.02-0.2:0.1-0.3:0.06-0.3, preferably 1:0.001-0.05:0.2: 0.2: 0.15.

As a further improvement, the reaction temperature of the invention is 0° C.~room temperature.

As a further improvement, after the reaction of the invention is completed, the obtained crude product is treated to obtain the chiral alkyl compound shown in Formula II. The treatment method includes thin-layer chromatography, column chromatography or vacuum distillation, preferably column chromatography.

The catalyst $FeX_2$-8-OIQ complex (8-OIQ: 8-oxazoline iminoquinoline ligand) used in the invention is an optically pure compound shown in Formula IV or its enantiomer or racemate. In Formula IV, $R^9$ is $C_1$~$C_{12}$ alkyl which is unsubstituted or substituted by 1 or 2 $C_1$~$C_4$ alkoxys, $C_5$~$C_{12}$ cycloalkyl which is unsubstituted or substituted by 1-3 substituents a, or aryl a which is unsubstituted or substituted by 1-4 substituents b; the aryl a is benzyl, phenyl or naphthyl; the substituent a is $C_1$~$C_4$ alkyl or $C_1$~$C_4$ alkoxy; and the substituent b is $C_1$~$C_4$ alkyl, $C_1$~$C_4$ alkoxy, $C_1$~$C_4$ fluoroalkyl, Cl~$C_4$ fluoroalkoxy, F or Cl;

$R^{10}$ is H, $C_1$~$C_{12}$ alkyl which is unsubstituted or substituted by 1-2 $C_1$~$C_4$ alkoxy, $C_5$~$C_{12}$ cycloalkyl which is unsubstituted or substituted by 1-3 substituents a, or aryl b which is unsubstituted or substituted by 1-3 substituents b; the aryl b is phenyl or naphthyl; the substituent a is $C_1$~$C_4$ alkyl or $C_1$~$C_4$ alkoxy; and the substituent b is $C_1$~$C_4$ alkyl, $C_1$~$C_4$ alkoxy, $C_1$~$C_4$ fluoroalkyl, $C_1$~$C_4$ fluoroalkoxy, F or Cl;

$R^{11}$, $R^{12}$, $R^{13}$, $R^{14}$ and $R^{15}$ are independently H, $C_1$~$C_{12}$ alkyl, $C_1$~$C_4$ fluoroalkoxy, F, Cl, nitro or $C_5$~$C_{12}$ cycloalkyl which is unsubstituted or substituted by 1-3 substituents a;

$R^{16}$ and $R^{17}$ are independently H, $C_1$~$C_{12}$ alkyl which is unsubstituted or substituted by 1-2 $C_1$~$C_4$ alkoxy groups, $C_5$~$C_{12}$ cycloalkyl which is unsubstituted or substituted by 1-3 substituents a, or aryl a which is unsubstituted or substituted by 1-3 substituents b;

$R^{18}$ is a $C_1$~$C_{12}$ alkyl group that is not substituted or substituted by 1-2 $C_1$~$C_4$ alkoxy groups, a cycloalkyl group of $C_5$~$C_{12}$ that is not substituted or substituted by 1-3 substituents a, or an aryl a that is not substituted or substituted by 1-3 substituents b;

In Formula IV, * represents a chiral carbon atom.

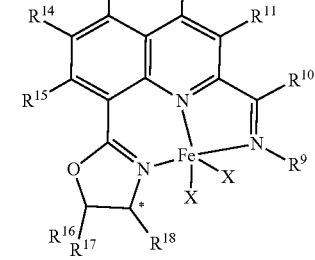

IV

X is F, Cl, Br, I, OAc or $CF_3SO_3$, preferably Cl or Br.

Further, the catalyst $FeX_2$-8-OIQ complex is preferably a compound shown in Formula IV, wherein $R^{11}$, $R^{12}$, $R^{13}$, $R^{14}$, $R^{15}$, $R^{16}$ and $R^{17}$ are preferably H; $R^{10}$ is preferably $C_1$~$C_4$ alkyl or diphenylmethylene; preferably, $R^9$ is $C_1$~$C_4$ alkyl, benzyl, phenyl or 2,6-diisopropylphenyl; preferably, $R^{18}$ is $C_1$~$C_4$ alkyl, benzyl or phenyl; X is Cl or Br.

Furthermore, the used chiral $FeX_2$-8-OIQ complex is preferably shown in Formula IV-1 or Formula IV-2

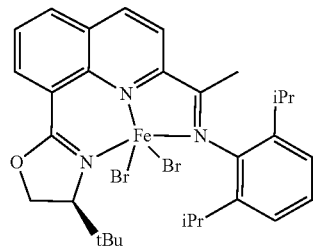

IV-1

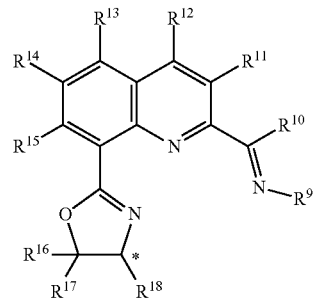

IV-2

In the invention, the compound shown in Formula IV can be prepared by the following method:

under nitrogen protection, a chiral iminoquinoline oxazoline compound shown in formula (1) react with ferrous salt $FeX_2$ in an organic solvent for 1-10 hours to prepare the complex shown in formula IV; the organic solvent is tetrahydrofuran or 2-methyltetrahydrofuran;

(1)

$R^9$ ~$R^{18}$ and * in formula (1) are all as described previously.

The mole ratio of the chiral iminoquinoline oxazoline compound shown in formula (1) and ferrous salt $FeX_2$ is 2.2-0.9:1, preferably 1.1-0.9:1, more preferably 1.1-1:1.

The synthesis of metal compounds shown in Formula IV can be carried out at low or high temperatures, such as $-20$~$150°$ C., preferably at room temperature.

The chiral iminoquinoline oxazoline compounds shown in formula (1) can be prepared by the following method:

(a) a 2-acyl-8-bromoquinoline compound shown in formula (2) and an amine compound shown in formula (3) are subjected to condensation reaction under the action of a catalyst to obtain a compound shown in formula (4);

(b) under the protection of nitrogen, the compound shown in formula (4) and an oxazoline compound shown in formula (5) are subjected to coupling reaction under the catalysis of a transition metal inorganic salt, an organic phosphine ligand and an inorganic base to obtain the chiral iminoquinoline oxazoline compound shown in formula (1);

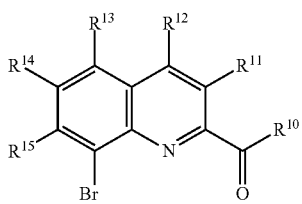

(2)

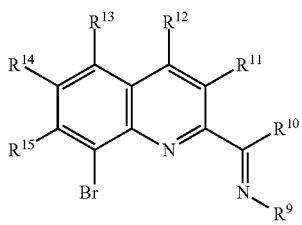

(3)

(4)

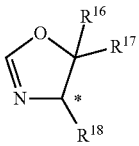

(5)

$R^9$~$R^{18}$ and * are as previously described.

In step (a), the mole ratio of the 2-acyl-8-bromoquinoline compound shown in formula (2) and amine compound shown in formula (3) is 1:1-10, preferably 1:1-5, more preferably 1:1-2.

The step (a) is carried out under the action of catalyst. The catalyst is proton acid or molecular sieve, preferably p-toluenesulfonic acid. The amount of the catalyst material is 1-5mol % of the 2-acyl-8-bromoquinoline compound shown in formula (2).

The reaction solvent of step (a) is an organic solvent, preferably toluene, benzene or xylene, more preferably toluene.

The reaction in step (a) needs to be heated to reflux, a water separator is used to separate water during reaction, and reaction time is 15-30 hours.

Step (b) is a coupling reaction catalyzed by the inorganic salt of transition metal Ru, Rh, Pd, Ir, organic phosphine ligand and inorganic base.

The step (b) is carried out under the catalysis of the transition metal inorganic salt, organic phosphine ligand and inorganic base. The transition metal inorganic salt refer to inorganic salt of Ru, Rh, Pd and Ir, preferably palladium acetate. The inorganic base is preferably lithium tert butyl alcohol; the organic phosphine ligand is preferably 1,2-bis (diphenylphosphine) ethane.

In step (b), the mole ratio of the compound shown in formula (4), the oxazoline compound shown in formula (5), the transition metal inorganic salt, the organic phosphorus ligand and the inorganic base is 1:1-5: 0.01-1: 0.02-2: 2-10, preferably 1:1-3: 0.01-0.1: 0.02-0.1: 2-4.

The step (b) is carried out in an organic solvent, which is any one of benzene, carbon tetrachloride, petroleum ether, tetrahydrofuran, dimethylformamide, ether, dichloromethane, trichloromethane, toluene, xylene, cyclohexane, n-hexane, n-heptane, dioxane and acetonitrile, preferably dioxane. The reaction temperature is −0° C. to 150° C., preferably heated to reflux for reaction, and reaction time is 1 hour to 48 hours.

The invention provides an effective method for synthesizing enantiopure alkane compounds from 1,1-disubstituted olefins and atmospheric hydrogen with high enantioselectivity, using $FeX_2$-8-OIQ complex, especially chiral $FeX_2$-8-OIQ complex as catalyst, silane compound and acetonitrile as co catalyst.

Compared with the previous methods of asymmetric hydrogenation of alkenes, this method is applicable to a variety of different types of olefins. The synthesis of substrate of the olefins is very simple. The method of the present invention has mild reaction conditions, simple operation, and high atom economy. In addition, the reaction does not require the addition of any other toxic transition metal salts (such as ruthenium, rhodium, palladium, etc.), and has great practical application value in the synthesis of drugs and materials. The invention can perform selective catalytic hydrogenation of the polyolefin using a large resistance catalyst. The conversion rate of the reaction of the present invention is good, generally reaching >99%, and the enantiomer selectivity is also high, generally being 70%-99%.

DETAILED DESCRIPTION

The technical scheme of the invention is further described in detail by specific embodiments, but the protection scope of the invention is not limited to this.

The catalyst used in the embodiment is shown below, and the compound shown in Formula IV-1 is referred to as $FeCl_2$-8-OIQ for short.

The preferred amount of metal complex is 0.001-10 mol %, more preferably 0.1-5 mol %.

Figure 1:
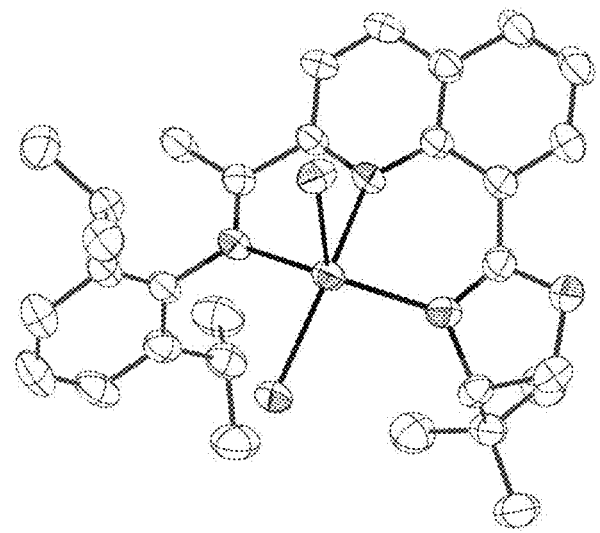
FIG. 1: X-ray diffraction spectrogram of the catalyst of formula IV-2.

The X-ray diffraction spectrogram of Formula IV-2 is shown in FIG. 1, CCDC Number: 2011869.

The catalyst synthesis route is as follows:

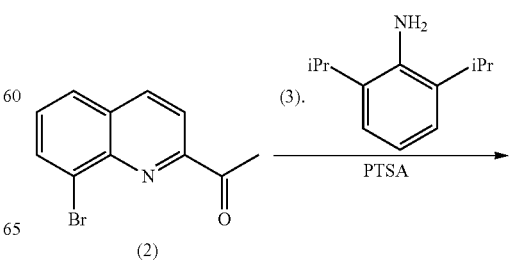

-continued

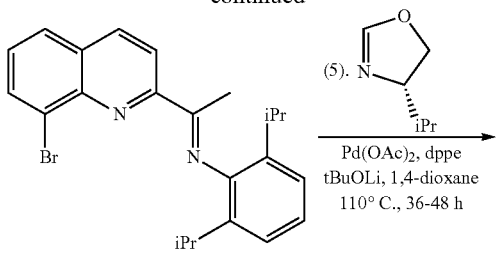

(4)-S

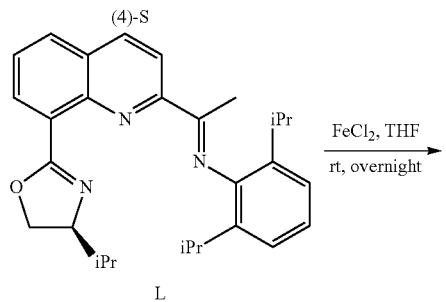

L

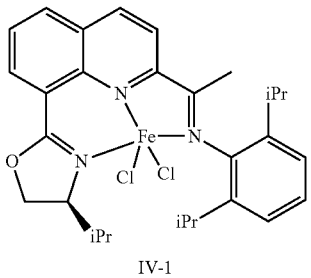

IV-1

The synthesis steps of the catalyst are as follows. The amine compounds shown in Formula (3) are commercially available, and the 2-acyl-8-bromoquinoline compounds shown in Formula (2) are prepared in accordance with the literature (K. Żukowska, E. Pump, A. E. Pazio, K. Woźniak, L. Cavallo, C. Slugovc Beilstein J. Org. Chem. 2015, 11, 1458.) o Oxazoline compounds shown in Formula (5) are synthesized according to the literature (J. Chen, T. Xi, Z. Lu Org. Chem. Front., 2018, 5, 247.).

Preparation of 8-bromo-2-acetylquinoline (2)

Under the protection of nitrogen, the 8-bromo-formylquinoline (6.9451 g, 29.3 mmol, 1.0 equiv) and ethyl ether (147 ml) were added in three necked flask (250 mL). Then methyl magnesium bromide (3 M in hex 12.7 mL 1.3 equiv) was dropped at 0° C. After dropping, the reaction stirred in room temperature for 12 hours. The mixture was quenched with saturated aqueous ammonium chloride solution (10 mL). The aqueous layer was separated and extracted with ether (3 times). The organic layers were combined, dried over anhydrous $Na_2SO_4$, filtered and concentrated in vacuo. The crude material was concentrated and diluted with dichloromethane, 22.31 g of PDC (pyridinium dichromate 58.8 mmol, 2.0 equiv) and silica gel (23.10 g) were added in reaction and stirring overnight at room temperature. After the reaction conducted, the solid was filtered and wash with dichloromethane, concentrated in vacuo to obtain a yellow solid, The crude material was subsequently purified via column chromatography on silica gel to afford the 8-bromo-2-acetylquinoline with white solid (17.4 mmol, 4.3615 g, 59% yield).

$^1$H NMR (400 MHz, $CDCl_3$) δ 8.07-7.99 (m, 2H), 7.93 (d, J=8.0 Hz, 1H), 7.65-7.58 (m, 1H), 7.56 (d, J=8.8 Hz, 1H), 2.96 (s, 3H); the data is consistent with the literature [S. Nagy, L. N. Winslow, S. Mihan; L. Lukesova, E. Nifant'ev, P. V. Ivchenko, V. Bagrov, US Patent 2012/0016092 2012.]

Preparation of 8-bromo-2-iminoquinoline (4)-S 2,6-Diisopropylaniline (4.2516 g, 24 mmol, 1.2 equiv) ᅳj 8-Bromo-2-acetylquinoline (5.0 g, 20 mmol, 1.0 equiv) were added in toluene (50 mL), then P-toluenesulfonic acid monohydrate (0.0761 g, 0.40 mmol, 2 mol %) was added, the mixtures was refluxed for 24 h and the water was separated by water separator, then the crude product was recrystallized with ethanol to afford the (4)-S with 7.3078 g (17.9 mmol, 90% yield). IR (neat): 2959, 2924, 1696, 1643, 1493, 1462, 1362 $cm^{-1}$; 1H NMR: (400.0 MHz, $CDCl_3$) δ 8.60 (d, J=8.8 Hz, 1H), 8.24 (d, J=8.4 Hz, 1H), 8.10 (d, J=7.2 Hz, 1H), 7.86 (d, J=8.0 Hz, 1H), 7.46 (dd, J=8.0,7.6 Hz, 1H), 7.22-7.17 (m, 2H), 7.15-7.10 (m, 1H), 2.80-2.72 (m, 2H), 2.43 (s, 3H), 1.17 (d, J=3.2 Hz, 6H), 1.15 (d, J=3.2 Hz, 6H); 13C NMR: (100.6 MHz, $CDCl_3$) δ 167.3, 156.5, 146.5, 144.3, 136.6, 135.5, 133.1, 130.0, 127.8, 127.4, 125.9, 123.7, 123.0, 119.4, 28.3, 23.2, 22.8, 16.9; HRMS (ESI) calculated for $[C23H26BrN2]+$ (M+H+), requires m/z 409.1279, found m/z 409.1290.

Synthesis of Ligand L

Under nitrogen, (4)-S (1.0213 g, 2.52 mmol, 1 equiv) and (S)-isopropyl oxazoline (0.3821 g, 3.375 mmol, 1.35 equiv) were added in dioxane (15 mL), $Pd(OAc)_2$ (0.0281 g, 0.0125 mmol, 5 mol %), dppe(0.0558 g, 0.14 mmol, 5.6 mol %), tBuOLi (0.4005 g, 5 mmol, 2 equiv) were added into the system, respectively. The reaction was degassed three times and stirred in 110° C. for 41 h, The crude material was subsequently purified via column chromatography on silica gel to afford the ligand L with 0.8456 g (1.9 mmol, 76% yield).

Synthesis of Iron Catalyst:

A 50 mL Schleck flask was charged with 0.95 eq. of $FeCl_2$, THF (0.1 M) and a solution of 1.0 eq. of (S)-La in THF under atmosphere of nitrogen. The mixture was stirred at room temperature for 17 h. The solvent was removed in vacuo. The resulting mixture was washed with ether and filtered under air. The cake was washed with ether and dried in vacuo to afford IV-1 and IV-2.

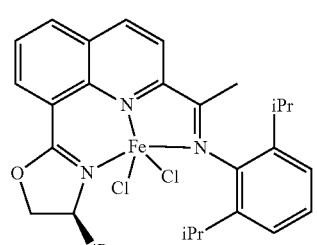

IV-1

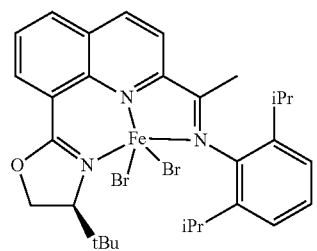

IV-2

Example 1 the FeX$_2$-8-OI-Catalyzed Asymmetric Hydrogenation of 1,1-Disubstituted Alkenes General procedure for asymmetric hydrogenation of 1,1-disubstituted alkenes: A 25 mL flame-dried Schleck flask was cooled at room temperature under nitrogen, charged with LeFeCl$_2$ (0.025 mmol), alkene (0.50 mmol), hydrosilane (0.10 mmol), the system was purged one time, The acetonitrile (0.10 mmol) and dry toluene (1 mL) were added successively, then NaBHEt3 (1 M in THF) (75 μL, 0.075 mmol) was injected slowly, the reaction was stirred 5 min, a balloon with hydrogen was added and the system was purged three times. The mixture was stirred for 12 hours in room temp. The reaction was quenched by PE. The mixture was filtered through a pad of silica gel and washed with PE (50 mL). The filtrate was concentrated without further purification to afford the corresponding product.

II-1: (R)-1-(sec-butyl)-4-methoxybenzene

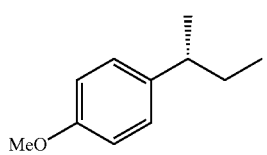

A colorless oil, >99% conversion. Optical Rotation: $[\alpha]_{20}^{D}=-23.2$ (c 1.11, CHCl$_3$), 99% ee. $^1$H NMR: (400.0 MHz, CDCl$_3$) δ 7.10 (d, J=8.4 Hz, 2H), 6.84 (d, J=8.4 Hz, 2H), 3.79 (s, 3H), 2.59-2.50 (m, 1H), 1.61-1.49 (m, 2H), 1.21 (d, J=7.2 Hz, 3H), 0.81 (t, J=7.6 Hz, 3H).

II-2: (R)-1-(benzyloxy)-4-(sec-butyl)benzene

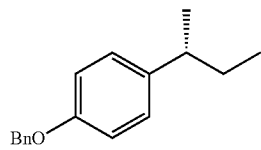

A colorless oil, >99% conversion. Optical Rotation: $[\alpha]^{20}_{D}=-8.6$ (c 1.35, CHCl$_3$). 98% ee. IR (neat): 2961, 2925, 1510, 1488 cm$^{-1}$; $^1$H NMR: (400.0 MHz, CDCl$_3$) δ 7.45-7.30 (m, 5H), 7.10 (d, J=8.8 Hz, 2H), 6.91 (d, J=8.4 Hz, 2H), 5.04 (s, 2H), 2.59-2.51 (m, 1H), 1.60-1.52 (m, 2H), 1.21 (d, J=6.8 Hz, 3H), 0.82 (t, J=7.2 Hz, 3H); $^{13}$C NMR: (100.0 MHz, CDCl$_3$) δ 156.9, 140.1, 137.3, 128.5, 127.9, 127.8, 127.5, 114.5, 70.0, 40.8, 31.3, 22.0, 12.2; HRMS (EI) calculated for [C$_{17}$H$_{20}$O]$^+$ requires m/z 240.1514, found m/z 240.1516.

II-3: (R)-2-(4-(sec-butyl)phenyl)-4,4,5,5-tetramethyl-1,3,2-dioxaborolane

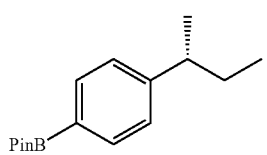

Figure 2:
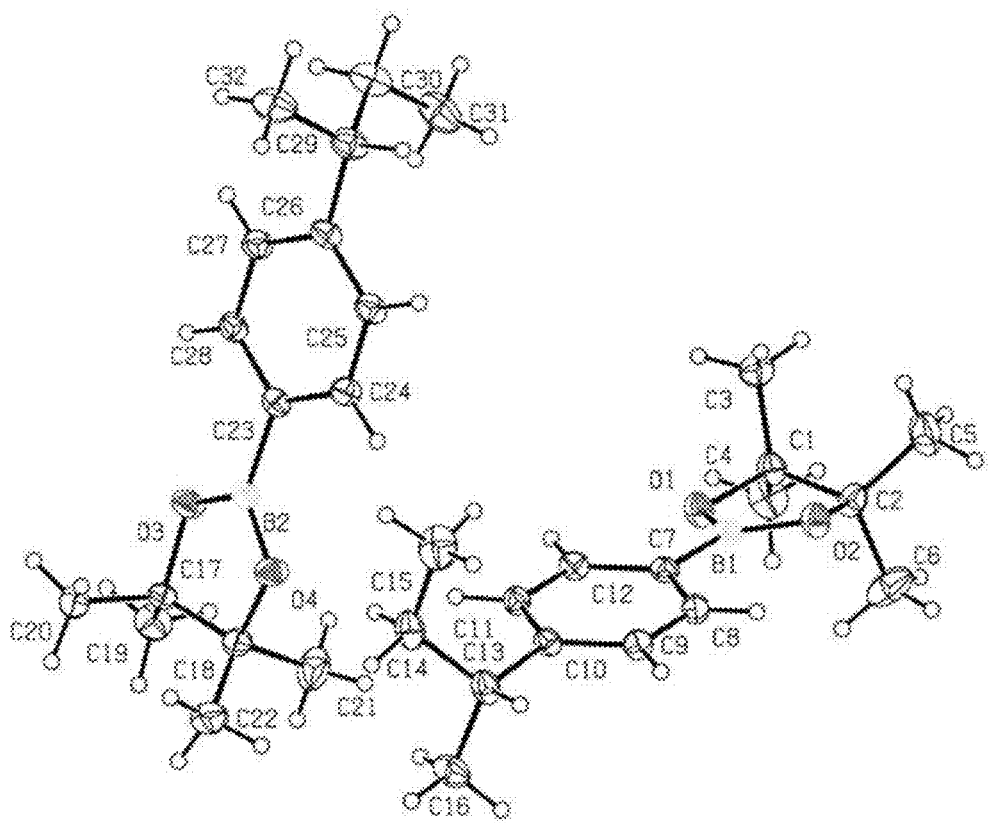
FIG. 2: X-ray diffraction spectrogram of the asymmetric hydrogenation product of formula II-3.

A colorless oil, >99% conversion. Optical Rotation: $[\alpha]^{20}_{D}=-2.1$ (c 1.18, CHCl$_3$). 94.4% ee, IR (neat): 2960, 2855, 1611, 1401, 1362, 1145 cm$^{-1}$; $^1$H NMR: (400.0 MHz, CDCl$_3$) δ 7.75 (d, J=8.0 Hz, 2H), 7.19 (d, J=8.0 Hz, 2H), 2.65-2.55 (m, 1H), 1.65-1.55 (m, 2H), 1.33 (s, 12H), 1.23 (d, J=6.8 Hz, 3H), 0.81 (t, J=7.6 Hz, 3H); $^{13}$C NMR: (100.0 MHz, CDCl$_3$) δ 151.1, 134.8, 126.5, 83.6, 41.9, 31.0, 24.8, 21.7, 12.2; HRMS (EI) calculated for [C$_{16}$H$_{25}$O$_2$B]$^+$ requires m/z 260.1948, found m/z 260.1949. The x-ray diffraction was added in FIG. 2. CCDC number: 2055703.

II-4: (R)-(4-(sec-butyl)phenyl)(methyl)sulfane

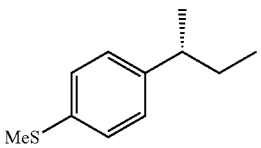

A colorless oil, >99% conversion. Optical Rotation: $[\alpha]^{20}_{D}=-18.1$ (c 1.03, CHCl$_3$). 95.1% ee, IR (neat): 2960, 2923, 1561, 1494, 1458, 1144 cm$^{-1}$; $^1$H NMR: (400.0 MHz, CDCl$_3$) δ 7.21 (d, J=8.0 Hz, 2H), 8.3 (d, J=8.0 Hz, 2H), 2.60-2.51 (m, 1H), 2.47 (s, 3H), 1.61-1.54 (m, 2H), 1.21 (d, J=6.8 Hz, 3H), 0.81 (t, J=7.6 Hz, 3H); $^{13}$C NMR: (100.6 MHz, CDCl$_3$) δ 144.9, 135.0, 127.6, 127.1, 41.2, 31.1, 21.8, 16.3, 12.2; HRMS (EI) calculated for [C$_{11}$H$_{16}$S]$^+$ requires m/z 180.0973, found m/z 180.0974.

II-5: (R)-5-(sec-butyl)benzo[d][1,3]dioxole

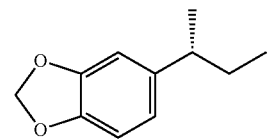

A colorless oil, >99% conversion. Optical Rotation: $[\alpha]^{20}_{D}=-12.8$ (c 0.30, CHCl$_3$). 98.6% ee, $^1$H NMR: (400.0 MHz, CDCl$_3$) δ 7.11-7.06 (m, 5H), 2.60-2.51 (m, 1H), 2.32 (s, 3H), 1.61-1.52 (m, 2H), 1.22 (d, J=6.8 Hz, 3H), 0.82 (t, J=7.2 Hz, 3H). IR (neat): 2961, 2927, 1487, 1440, 1249 cm$^{-1}$; $^1$H NMR: (400.0 MHz, CDCl$_3$) δ 6.73 (d, J=8.0 Hz, 1H), 6.68 (s, 1H), 6.62 (d, J=8.0 Hz, 1H), 5.92 (s, 2H), 2.57-2.47 (m, 1H), 1.60-1.48 (m, 2H), 1.19 (d, J=6.8 Hz, 3H), 0.81 (t, J=7.2 Hz, 3H); $^{13}$C NMR: (100.0 MHz, CDCl$_3$) δ 147.5, 145.4, 141.7, 119.9, 107.9, 107.2, 100.7, 41.5, 31.3, 22.1, 12.2; HRMS (EI) calculated for [C$_{11}$H$_{14}$O$_2$]$^+$ requires m/z 178.0994, found m/z 178.0992.

II-6: (R)-1-(sec-butyl)-4-fluorobenzene

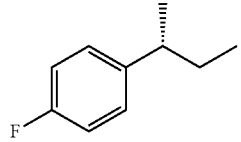

A colorless oil, >99% conversion. Optical Rotation: $[\alpha]^{20}_{D}=-12.7$ (c 1.25, CHCl$_3$). 92.1% ee. $^1$H NMR: (400.0 MHz, CDCl$_3$) δ 7.16-7.09 (m, 2H), 7.00-6.92 (m, 2H), 2.63-2.53 (m, 1H), 1.61-1.51 (m, 2H), 1.21 (d, J=6.8 Hz, 3H), 0.80 (t, J=7.2 Hz, 3H); $^{13}$C NMR: (100.6 MHz, CDCl$_3$) δ 161.1 (d, J=241.3 Hz), 143.2 (d, J=2.9 Hz), 128.3 (d, J=7.3 Hz), 114.9(d, J=20.4 Hz), 41.0, 31.3, 22.0, 12.1; $^{19}$F NMR: (376 MHz, CDCl$_3$) δ-118.1.

II-7: (R)-1-(sec-butyl)-4-chlorobenzene

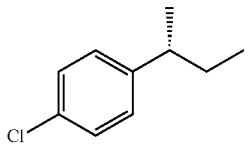

A colorless oil, >99% conversion. Optical Rotation: $[\alpha]^{20}_D=-3.2$ (c 1.37, CHCl$_3$). 94.3% ee, IR (neat): 2958, 2925, 2855, 1493, 1461, 1378 cm$^{-1}$; $^1$H NMR: (400.0 MHz, CDCl$_3$) δ 7.25 (d, J=8.4 Hz, 2H), 7.10 (d, J=8.4 Hz, 2H), 2.61-2.53 (m, 1H), 1.62-1.51 (m, 2H), 1.21 (d, J=6.8 Hz, 3H), 0.80 (t, J=7.2 Hz, 3H); $^{13}$C NMR: (100.6 MHz, CDCl$_3$) δ 146.1, 131.3, 128.4, 128.3, 41.1, 31.1, 21.8, 12.1; HRMS (EI) calculated for [C$_{10}$H$_{13}$Cl]$^+$ requires m/z 168.0706, found m/z 168.0706.

II-8: (R)-1-(sec-butyl)-3-methoxybenzene

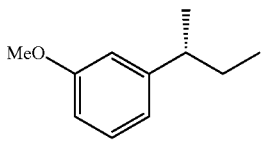

A colorless oil, >99% conversion. Optical Rotation: $[\alpha]^{20}_D=-21.4$ (c 0.97, CHCl$_3$). 95.4% ee, IR (neat): 2960, 2922, 1604, 1487, 1458, 1261 cm$^{-1}$; $^1$H NMR: (400.0 MHz, CDCl$_3$) δ 7.21 (t, J=7.8 Hz, 1H), 6.79-6.72 (m, 3H), 3.80 (s, 3H), 2.61-2.52 (m, 1H), 1.64-1.00 (m, 2H), 1.23 (d, J=6.8 Hz, 3H), 0.83 (t, J=7.2 Hz, 3H); $^{13}$C NMR: (100.0 MHz, CDCl$_3$) δ 159.6, 149.5, 129.1, 119.5, 113.0, 110.7, 55.1, 41.7, 31.1, 21.8, 12.2; HRMS (EI) calculated for [C$_{11}$H$_{16}$O]$^+$ requires m/z 164.1201, found m/z 164.1203.

II-9: (R)-1-(sec-butyl)-2-methoxybenzene

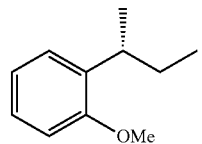

A colorless oil, >99% conversion. Optical Rotation: $[\alpha]^{20}_D=-1.4$ (c 0.51, CHCl$_3$). 77.4% ee, IR (neat): 2921, 2853, 1511, 1464, 1380, 1246 cm$^{-1}$; $^1$H NMR: (400.0 MHz, CDCl$_3$) δ 7.19-7.12 (m, 2H), 6.95-6.82 (m, 2H), 3.81 (s, 3H), 3.16-3.04 (m, 1H), 1.70-1.54 (m, 2H), 1.19 (d, J=6.8 Hz, 3H), 0.84 (t, J=6.8 Hz, 3H); $^{13}$C NMR: (100.6 MHz, CDCl$_3$) δ 157.1, 135.9, 126.7, 126.4, 120.5, 110.4, 55.3, 33.4, 29.8, 20.4, 12.1; HRMS (EI) calculated for [C$_{11}$H$_{16}$O]$^+$ requires m/z 164.1201, found m/z 164.1202.

II-10: (R)-5-(sec-butyl)-1-methyl-1H-indole

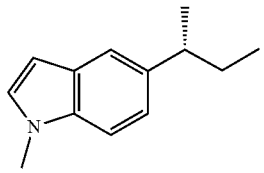

A colorless oil, >99% conversion. Optical Rotation: $[\alpha]^{20}_D=-16.0$ (c 1.11, CHCl$_3$). 97.9% ee, IR (neat): 2958, 2919, 1513, 1490 1450, 1352 cm$^{-1}$; $^1$H NMR: (400.0 MHz, CDCl$_3$) δ 7.42 (s, 1H), 7.28-7.23 (m, 1H), 7.07 (d, J=7.6 Hz, 1H), 7.01 (d, J=2.8 Hz, 1H), 6.42 (d, J=2.8 Hz, 1H), 3.77 (s, 3H), 2.74-2.63 (m, 1H), 1.71-1.59 (m, 2H), 1.29 (d, J=6.8 Hz, 3H), 0.83 (t, J=7.2 Hz, 3H); $^{13}$C NMR: (100.0 MHz, CDCl$_3$) δ 138.6, 135.4, 128.7, 128.5, 121.1, 118.6, 108.8, 100.5, 41.7, 32.7, 31.6, 22.6, 12.4; HRMS (EI) calculated for [C$_{13}$H$_{17}$N]$^+$ requires m/z 187.1361, found m/z 187.1362.

II-11: (R)-1-(hexan-2-yl)-4-methoxybenzene

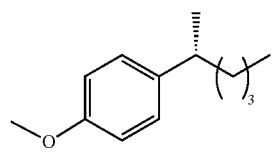

A colorless oil, >99% conversion. Optical Rotation: $[\alpha]^{20}_D=-27.4$ (c 0.89, CHCl$_3$). 93.9% ee, IR (neat): 2957, 2927, 1611, 1512, 1461, 1247 cm$^{-1}$; $^1$H NMR: (400.0 MHz, CDCl$_3$) δ 7.10 (d, J=8.8 Hz, 2H), 6.83 (d, J=8.8 Hz, 2H), 3.79 (s, 3H), 2.67-2.57 (s, 1H), 1.56-1.48 (m, 2H), 1.34-1.07 (m, 7H), 0.85 (t, J=6.8 Hz, 3H); $^{13}$C NMR: (100.0 MHz, CDCl$_3$) δ 157.6, 140.1, 127.8, 113.6, 55.2, 39.0, 38.3, 29.9, 22.8, 22.5, 14.0; HRMS (EI) calculated for [C$_{13}$H$_{20}$O]$^+$ requires m/z 192.1514, found m/z 192.1514.

II-12: (R)-1-(heptan-2-yl)-4-methoxybenzene

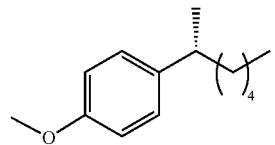

A colorless oil, >99% conversion. Optical Rotation: $[\alpha]^{20}_D=-26.7$ (c 0.75, CHCl$_3$). 94.8% ee, IR (neat): 2923, 2854, 1612, 1512, 1461, 1375 cm$^{-1}$; $^1$H NMR: (400.0 MHz, CDCl$_3$) δ 7.09 (d, J=8.8 Hz, 2H), 6.83 (d, J=8.4 Hz, 2H), 3.79 (s, 3H), 2.67-2.57 (m, 1H), 1.55-1.47 (m, 2H), 1.30-1.10 (m, 9H), 0.85 (t, J=6.4 Hz, 3H); $^{13}$C NMR: (100.0 MHz, CDCl$_3$) δ 157.6, 140.1, 127.7, 113.6, 55.1, 39.0, 38.6, 31.9, 27.4, 22.6, 22.5, 14.1; HRMS (EI) calculated for [C$_{14}$H$_{22}$O]$^+$ requires m/z 206.1671, found m/z 206.1672.

II-13: (R)-1-methoxy-4-(octan-2-yl)benzene

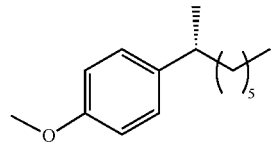

A colorless oil, >99% conversion. Optical Rotation: $[\alpha]^{20}_D=-23.4$ (c 1.20, CHCl$_3$). 90.8% ee, IR (neat): 2955, 2854, 1612 1512, 1461, 1375 cm$^{-1}$; $^1$H NMR: (400.0 MHz, CDCl$_3$) δ 7.09 (d, J=8.8 Hz, 2H), 6.83 (d, J=8.4 Hz, 2H), 3.79 (s, 3H), 2.67-2.57 (m, 1H), 1.56-1.48 (m, 2H), 1.30-1.10 (m, 11H), 0.85 (t, J=6.4 Hz, 3H); $^{13}$C NMR: (100.0 MHz, CDCl$_3$) δ 157.6, 140.1, 127.7, 113.6, 55.1, 39.1, 38.6, 31.8, 29.4, 27.7, 22.6, 22.5, 14.1; HRMS (EI) calculated for [C$_{15}$H$_{24}$O]$^+$ requires m/z 220.1827, found m/z 220.1826.

II-14: (R)-N,N-dimethyl-4-(p-tolyl)pentan-1-amine

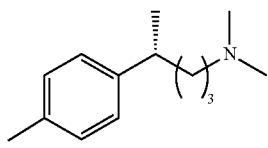

A colorless oil, >99% conversion. Optical Rotation: $[\alpha]^{20}_D=-17.4$ (c 0.92, CHCl$_3$). 96.6% ee, IR (neat): 2941, 2858, 2763, 1651, 1515, 1374 cm$^{-1}$; $^1$H NMR: (400.0 MHz, CDCl$_3$) δ 7.12-7.04 (m, 4H), 2.70-2.59 (m, 1H), 2.31 (s, 3H), 2.25-2.14 (m, 8H), 1.61-1.52 (m, 2H), 1.47-1.28 (m, 2H), 1.23 (d, J=6.8 Hz, 3H); $^{13}$C NMR: (100.0 MHz, CDCl$_3$) δ 144.4, 135.2, 128.9, 126.8, 59.8, 45.4, 39.5, 36.1, 25.8, 22.4, 20.9; HRMS (EI) calculated for [C$_{14}$H$_{23}$N]$^+$ requires m/z 205.1830, found m/z 205.1832.

II-15: (R)-propane-1,2-diyldibenzene

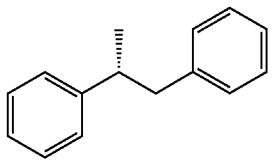

A colorless oil, >99% conversion. Optical Rotation: $[\alpha]^{20}_D=-33.9$ (c 1.09, CHCl$_3$). 84.3% ee, $^1$H NMR: (400.0 MHz, CDCl$_3$) δ 7.35-7.01 (m, 10H), 3.07-2.88 (m, 2H), 2.83-2.69 (m, 1H), 1.24 (d, J=6.8 Hz, 3H); $^{13}$C NMR: (100.0 MHz, CDCl$_3$) δ 147.0, 140.8, 129.1, 128.3, 128.1, 127.0, 126.0, 125.8, 45.0, 41.8, 21.1.

II-16: (1R,3R)-3-(4-((R)-sec-butyl)phenoxy)-1,7,7-trimethylbicyclo[2.2.1]heptane

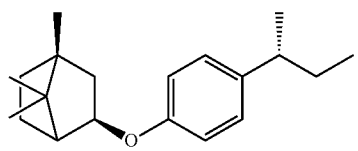 [SMILES: CC[C@@H](C)c1ccc(O[C@@H]2C[C@@]3(C)CCC2C3(C)C)cc1]

A colorless oil, >99% conversion. Optical Rotation: $[\alpha]^{20}_D=-88.3$ (c 0.79, CHCl$_3$). 96% ee, IR (neat): 2955, 2875, 1610, 1510, 1455, 1245 cm$^{-1}$; $^1$H NMR: (400.0 MHz, CDCl$_3$) δ 7.06 (d, J=8.8 Hz, 2H), 6.76 (d, J=8.8 Hz, 2H), 4.32-4.25 (m, 1H), 2.58-2.47 (m, 1H), 2.40-2.30 (m, 1H), 2.29-2.18 (m, 1H), 1.81-1.69 (m, 2H), 1.61-1.50 (m, 2H), 1.23-1.37 (m, 2H), 1.20 (d, J=7.2 Hz, 3H) 1.13 (dd, J=13.2, 3.2 Hz, 1H), 0.97-0.88 (m, 9H), 0.81 (t, J=7.2 Hz, 3H); $^{13}$C NMR: (100.0 MHz, CDCl$_3$) δ 157.2, 139.2, 127.7, 115.1, 82.7, 49.5, 47.5, 45.2, 40.8, 36.9, 31.3, 27.9, 26.8, 22.0, 19.7, 19.0, 13.8, 12.3. HRMS (EI) calculated for [C$_{20}$H$_{30}$O]$^+$ requires m/z 286.2297, found m/z 286.2297.

II-17: (R,E)-1-(sec-butyl)-4-((3,7-dimethylocta-2,6-dien-1-yl)oxy)benzene

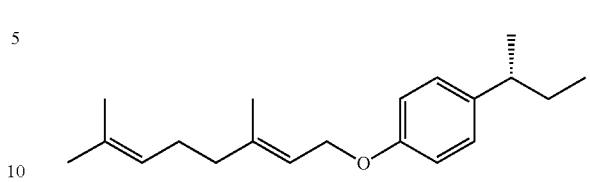

A colorless oil, >99% conversion. Optical Rotation: $[\alpha]^{20}_D=-13.1$ (c 0.78, CHCl$_3$). 97.2% ee, IR (neat): 2963, 2922, 1671, 1611, 1511, 1455 cm$^{-1}$; $^1$H NMR: (400.0 MHz, CDCl$_3$) δ 7.08 (d, J=8.8 Hz, 2H), 6.85 (d, J=8.4 Hz, 2H), 5.50 (t, J=6.8 Hz, 1H), 5.10 (t, J=5.2 Hz, 1H), 4.51 (d, J=6.8 Hz, 2H), 2.59-2.48 (m, 1H), 2.18-2.04 (m, 4H), 1.73(s, 3H),1.68 (s, 3H), 1.58 (s, 3H), 1.57-1.51 (m, 2H), 1.21 (d, J=6.8 Hz, 3H), 0.81 (t, J=7.6 Hz, 3H); $^{13}$C NMR: (100.0 MHz, CDCl$_3$) δ 157.0, 140.8, 139.6, 131.7, 127.8, 123.8, 119.8, 114.4, 64.8, 40.8, 39.5, 31.3, 26.3, 25.6, 22.0, 17.6, 16.6, 12.2. HRMS (EI) calculated for [C$_{20}$H$_{30}$O]$^+$ requires m/z 286.2297, found m/z 286.2298.

II-18: (R)-2-(3-(3-methoxy-4-methylphenyl)butyl)-1,3-dioxolane

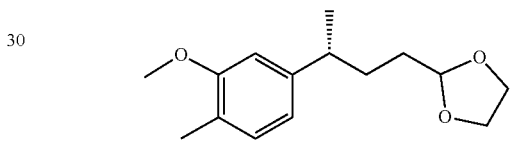

A colorless oil, >99% conversion. Optical Rotation: $[\alpha]^{\circ}_D=-11.4$ (c 1.98, CHCl$_3$). 97.2% ee, IR (neat): 2954, 2926, 1611, 1582, 1462, 1256 cm$^{-1}$; $^1$H NMR: (400.0 MHz, CDCl$_3$) δ 7.03 (d, J=7.6 Hz, 1H), 6.71-6.63 (m, 2H), 4.81 (t, J=4.8 Hz, 1H), 4.01-3.79 (m, 7H), 2.71-2.59 (m, 1H), 2.17 (s, 3H), 1.73-1.49 (m, 4H), 1.25 (d, J=7.2 Hz, 3H); 13C NMR: (100.0 MHz, CDCl3) δ 157.6, 146.1, 130.4, 124.0, 118.6, 108.8, 104.6, 64.8, 55.2, 39.9, 32.4, 32.1, 22.4, 15.8; HRMS (EI) calculated for [C$_{15}$H$_{22}$O$_3$]+ requires m/z 250.1569, found m/z 250.1569.

II-19: (R)-5-methyl-6,7,8,9-tetrahydro-5H-benzo[7]annulene

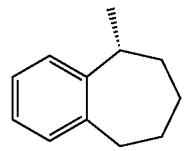

A colorless oil, >99% conversion. Optical Rotation: $[\alpha]^{20}_D=+10.6$ (c 0.50, CHCl$_3$). 90.5% ee, $^1$H NMR: (400.0 MHz, CDCl$_3$) δ 7.22-7.04 (m, 4H), 3.10-2.99 (m, 1H), 2.93-2.83 (m, 1H), 2.83-2.74 (m, 1H), 1.98-1.86 (m, 1H), 1.86-1.68 (m, 3H), 1.51-1.30 (m, 5H); $^{13}$C NMR: (100.0 MHz, CDCl$_3$) δ 146.5, 142.8, 129.2, 126.0, 125.6, 125.2, 37.7, 36.1, 36.0, 30.1, 27.8, 20.4.

II-20: (R) -1-(3,4-dimethylpentyl)-4-methoxybenzene

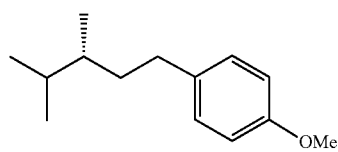

A colorless oil, 42% conversion. 54% ee. [1] H NMR: (400.0 MHz, CDCl$_3$) δ 7.10 (d, J=8.0 Hz, 2H), 6.82 (d, J=8.0 Hz, 2H), 3.79 (s, 3H), 2.66-2.55 (m, 1H), 2.53-2.41 (m, 1H), 1.69-1.56 (m, 2H), 1.44-1.25 (m, 2H), 0.93-0.77 (m, 9H).

Example 2

Selective Hydrogenation of 1,1-Disubstituted Olefins Using the Catalyst FeCl$_2$-8-OIQ (tBuoxazole Ring) with Large Steric Hindrance

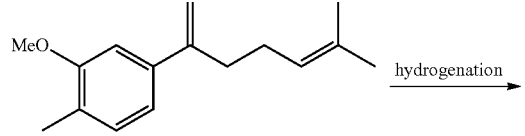

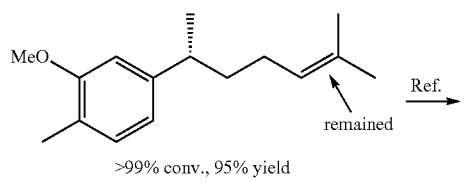

>99% conv., 95% yield
93% ee

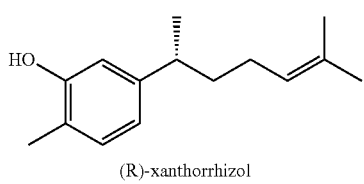

(R)-xanthorrhizol

A 25 mL flame-dried Schleck flask was cooled at room temperature under nitrogen, charged with LeFeCl$_2$ (0.025 mmol), alkene (0.50 mmol), hydrosilane (0.10 mmol), the system was purged one time, The acetonitrile (0.10 mmol) and dry toluene (1 mL) were added successively, then NaBHEt3 (1 M in THF) (75 μL, 0.075 mmol) was injected slowly, the reaction was stirred 5 min, a balloon with hydrogen was added and the system was purged three times. The mixture was stirred for 12 hours in room temp. The reaction was quenched by PE. The mixture was filtered through a pad of silica gel and washed with PE (50 mL). The filtrate was concentrated without further purification to afford the corresponding product with >99% conversion. Optical Rotation: $[α]^{20}_D$=−32.5 (c 1.75, CHCl$_3$). 93% ee. The (R)-xanthorrhizol could be synthesized according to the literature.

Example 3

Synthesis of Drug Intermediates

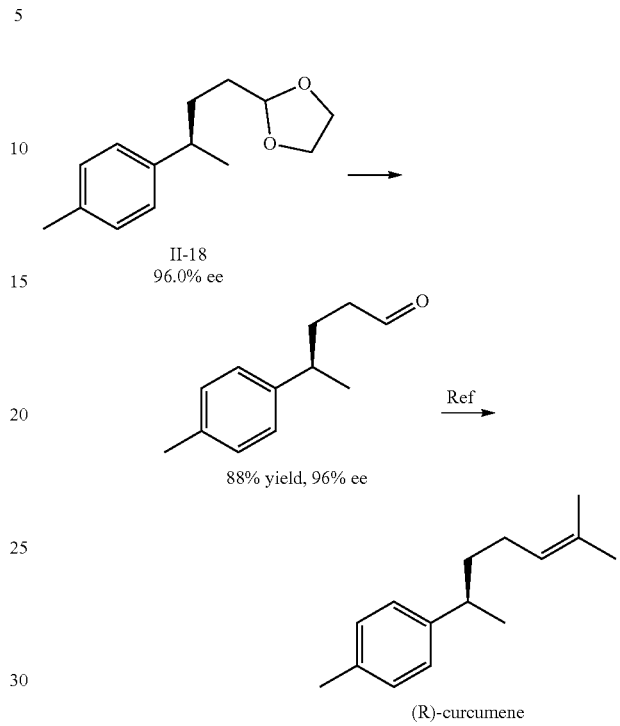

II-18
96.0% ee

88% yield, 96% ee (R)-curcumene

To (R)-2-(3-(p-tolyl)butyl)-1,3-dioxolane (II-18) (0.0404 g, 1 equiv) was added a solution of AcOH (6 ml) and H$_2$O (2 ml). The reaction mixture was stirred at 60° C. for 5 h and then was cooled down to room temperature. Adding the sodium hydroxide solution to adjust pH to 7, then exacted with ethyl acetate (3×10 mL), the solvent was removed in vacuo, providing the crude residue. The crude material was purified by column chromatography (PE/EA (30/1)) to give the intermediate of (R)-curcumene (0.0286 g, 88% yield) as a colorless oil. Optical Rotation: $[α]^{20}_D$=−33.9 (c 0.91, CHCl$_3$). 96% ee. Optical Rotation: $[α]^{20}_D$=−33.9 (c 0.91, CHCl$_3$). 96% ee, $^1$H NMR: (400.0 MHz, CDCl$_3$) δ 9.68 (t, J=1.6 Hz, 1H), 7.14-7.03 (m, 4H), 2.75-2.63 (m, 1H), 2.39-2.24 (m, 2H), 1.99-1.79 (m, 2H), 1.26 (d, J=7.2 Hz, 3H); $^{13}$C NMR: (100.6 MHz, CDCl$_3$) δ 202.4, 142.9, 135.7, 129.1, 126.8, 42.1, 38.8, 30.3, 22.3, 20.9. (: Song, S.; Zhu, S. -F.; Yang, S.; Li, S.; Zhou, Q. -L. Angew. Chem. Int. Ed. 2012, 51, 2708.)

Example 4

Comparative Experiment on Catalytic Performance and Reaction Conditions of Various Catalysts

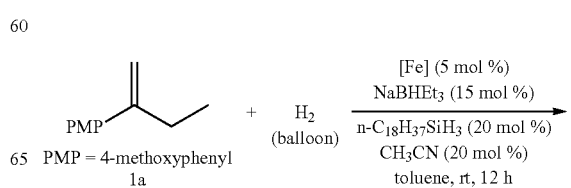

PMP = 4-methoxyphenyl
1a

-continued

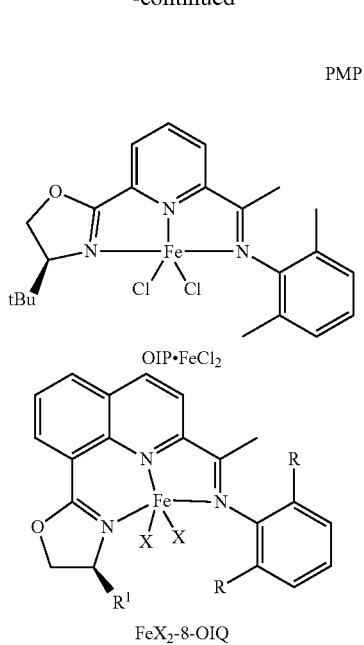

La•FeCl₂ R = Me, R¹ = tBu
Lb•FeCl₂ R = iPr, R¹ = tBu
Lb•FeBr₂ R = iPr, R¹ = tBu
Lc•FeCl₂ R = iPr, R¹ = Bn
Ld•FeCl₂ R = iPr, R¹ = iPr

| entry | cat. | yield of 2a (%)[b] | recovery of 1a (%) | isom. (%) | ee of 2a (%)[c] | Note |
|---|---|---|---|---|---|---|
| 1 | OIP•FeCl₂ | 25 | 51 | 24 | 58 | LP17107 |
| 2 | La•FeCl₂ | >99 | 0 | 0 | 88 | LP15115-B |
| 3 | Lb•FeCl₂ | 98 | 0 | 2 | 99 | LP15114-A |
| 4 | Lc•FeCl₂ | 98 | 0 | 2 | 97 | LP15115-A |
| 5 | Ld•FeCl₂ | >99 | 0 | 0 | 99 | LP17005 |

[a] The reactions were conducted using alkene (0.5 mmol), H₂ balloon, hydrosilane (20 mol %), CH₃CN (20 mol %), iron cat. (5 mol %), NaBHEt₃ (15 mol %), and toluene (1 mL) at rt for 12 h;
[b] The conversions and recoveries were determined by ¹H NMR using TMSPh as an internal standard; ee values were determined by GC using chiral column.

What is claimed is:

1. A method for preparing chiral alkyl compounds by asymmetric hydrogenation of olefins catalyzed by iron complex catalyst, wherein the method is as follows: reacting a disubstituted olefin shown in Formula I as a raw material, atmospheric hydrogen as hydrogen source, FeX2-8-OIQ complex as catalyst, hydrosilane and acetonitrile as co catalysts, for 12-24 hours under the activation of a reducing agent, to prepare a chiral alkyl compound shown in Formula II; wherein;

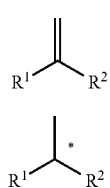

in Formula II, * represents a chiral carbon atom;

in Formula I or Formula II, $R^1$ is $C_2$~$C_8$ alkyl, naphthyl, a group shown in Formula III, or a N and O containing heterocyclic aryl group of $C_4$~$C_{10}$;

in $R^1$, the H on $C_2$~$C_8$ alkyl is not substituted or substituted by at least one substituent A, selected from the group consisting of and the substituent A is selected from the group consisting of phenyl, naphthyl, heterocyclic aryl or substituted phenyl; heterocyclic aryl is indolyl, pyridinyl, pyrrolyl, thiophenyl and furanyl; substituted phenyl is the phenyl group in which H on phenyl is replaced by at least one substituent B, and the substituent B is selected from the group consisting of $C_1$~$C_3$ alkyl, $C_1$~$C_3$ alkoxy, halogen and $C_1$~$C_3$ alkylthio;

in $R^1$, the N and O containing heterocyclic aryl group of $C_4$~$C_{10}$ is selected from the group consisting of pyridinyl, pyrrolyl, indolyl, benzodioxazolyl, benzoxazolyl and furanyl;

in $R^1$, the H on naphthyl and the N and O containing heterocyclic aryl group of $C_4$~$C_{10}$ are not substituted or substituted by at least one substituent C, and the substituent C is $C_1$~$C_3$ alkyl or $C_1$~$C_3$ alkoxy;

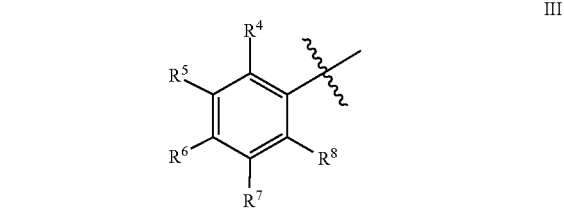

in $R^1$, among the groups shown in Formula III, $R^4$, $R^5$, $R^6$, $R^7$, $R^8$ are selected from the group consisting of H, halogen, $C_1$~$C_2$ alkyl, $C_1$~$C_3$ alkoxy, benzyloxy, $C_1$~$C_3$ alkylthio, tert butyl dimethyl siloxy, trifluoromethyl, dimethylamino, pinacol borate, d-borneoxy, citronellol oxy, menthol oxy or geraniol oxy, and when $R^4$, $R^5$, $R^6$, $R^7$, $R^8$ are all H, Formula III is phenyl; and halogen is F or Cl;

in Formula I or Formula II, $R^2$ is $C_1$~$C_8$ alkyl, $C_2$~$C_8$ alkenyl, phenyl or benzyl; the H on $C_1$~$C_8$ alkyl and $C_2$~$C_8$ alkenyl are not substituted or substituted by at least one substituent D selected from the group consisting of phenyl, substituted phenyl, $C_1$~$C_3$ amino or 1,3-dioxolacyl;

or in Formula I or Formula II, $R^1$ and $R^2$ are connected into a ring to form $C_9$~$C_{12}$ benzocycloalkyl; H on $C_9$~$C_{12}$ benzocycloalkyl is not substituted or substituted by at least one substituent E, and the substituent E is selected from the group consisting of $C_1$~$C_3$ alkyl, $C_1$~$C_3$ alkoxy or halogen;

$R^1$ and $R^2$ are different substituents; wherein the catalyst FeX2-OIQ complex is an optically pure compound shown in Formula IV or its enantiomer or racemate;

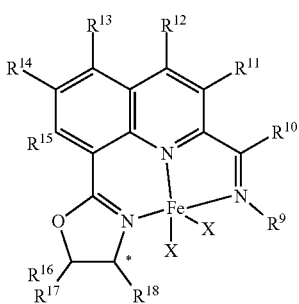

IV wherein in Formula IV, $R^9$ is C1-C12 alkyl which is unsubstituted or substituted by one or two C1-C4 alkoxy, C5-C12 cycloalkyl which is unsubstituted or substituted by one to three substituents A, or aryl A which is unsubstituted or substituted by 1-4 substituents B; the aryl A is selected from the group consisting of benzyl, phenyl and naphthyl; the substituent A is selected from the group consisting of C1-C4 alkyl and C1-C4 alkoxy; and the substituent B is selected from the group consisting of C1-C4 alkyl, C1-C4 alkoxy, C1-C4 fluoroalkyl, C1-C4 fluoroalkoxy, F and Cl;

$R^{10}$ is selected from the group consisting of H, C1-C12 alkyl which is unsubstituted or substituted by one or two C1-C4 alkoxy, C5-C12 cycloalkyl which is unsubstituted or substituted by 1-3 substituents A, or aryl B which is unsubstituted or substituted by 1-3 substituents A; the aryl B is phenyl or naphthyl; the substituent A is selected from the group consisting of C1-C4 alkyl and C1-C4 alkoxy; and the substituent B is selected from the group consisting of C1-C4 alkyl, C1-C4 alkoxy, C1-C4 fluoroalkyl, C1-C4 fluoroalkoxy, F and Cl;

$R^{11}$, $R^{12}$, $R^{13}$, $R^{14}$ and $R^{15}$ are independently selected from the group consisting of H, C1-C12 alkyl, C1-C4fluoroalkoxy, F, Cl, nitro and C5-C12 cycloalkyl which is unsubstituted or substituted by 1-3 substituents A; the substituent A is selected from the group consisting of C1-C4 alkyl and C1-C4 alkoxy; and the substituent B is selected from the group consisting of C1-C4 alkyl, C1-C4 alkoxy, C1-C4 fluoroalkyl, C1-C4 fluoroalkoxy, F and Cl;

$R^{16}$ and $R^{17}$ are independently selected from the group consisting of H and C1-C12 alkyl A which is unsubstituted or substituted by one or two C1-C4 alkoxy, C5-C12 cycloalkyl which is unsubstituted or substituted by 1-3 substituents A, or aryl A which is unsubstituted or substituted by 1-3 substituents B; the aryl A is selected from the group consisting of benzyl, phenyl and naphthyl;

the substituent A is selected from the group consisting of C1-C4 alkyl and C1-C4 alkoxy; and the substituent B is selected from the group consisting of C1-C4 alkyl, C1-C4 alkoxy, C1-C4 fluoroalkyl, C1-C4 fluoroalkoxy, F and Cl;

$R^{18}$ is selected from the group consisting of C1~C12 alkyl group that is not substituted or substituted by 1-2 C1~C4 alkoxy, C5-C12 cycloalkyl which is not substituted or substituted by 1-3 substituents A, or aryl A which is not substituted or substituted by 1-3 substituents B; the aryl A is selected from the group consisting of benzyl, phenyl and naphthyl; the substituent A is selected from the group consisting of C1-C4 alkyl and C1-C4 alkoxy; and the substituent B is selected from the group consisting of C1-C4 alkyl, C1-C4 alkoxy, C1-C4 fluoroalkyl, C1-C4 fluoroalkoxy, F and Cl;

in Formula IV,* represents a chiral carbon atom;

X is selected from the group consisting of F, Cl, Br, I, OAc and CF3SO3--;

and wherein the reducing agent is selected from the groups consisting of sodium triethylborohydride, sodium tri-sec-butyl-borohydride, lithium triethylborohydride, sodium tert-butoxide, potassium tert-butoxide, lithium tert-butoxide, sodium tert-pentoxide, sodium ethoxide, sodium methoxide and potassium methoxide.

2. The method according to claim 1, wherein $R^1$ is $C_2$~$C_8$ alkyl, naphthyl, 6-methoxynaphthalyl, pyridinyl, 2-methoxypyridyl, indolyl, N-methylindolyl, benzodioxazolyl and the group shown in Formula III;

in $R^1$, when $R^1$ is $C_2$~$C_8$ alkyl, H on $C_2$~$C_8$ alkyl is replaced by a substituent A, $R^1$ is selected from the group consisting of expressed as $R^A$—$(CH_2)_n$—, wherein n is an integer of 2 to 8, $R^A$ is a substituent A on the carbon chain, and $R^A$ is phenyl, naphthyl or p-methoxyphenyl;

the group shown in Formula III is phenyl or substituted phenyl with 1-2 substituents, and the substituent on the substituted phenyl is selected from the group consisting of halogen, $C_1$~$C_2$ alkyl, $C_1$~$C_3$ alkoxy, benzyloxy, $C_1$~$C_3$ alkylthio, tert-butyl dimethyl siloxy, trifluoromethyl, dimethylamino, pinacol borate, d-borneol, citronellol-oxyl, menthol-oxyl and geraniol-oxyl;

$R^2$ is selected from the group consisting of $C_2$~$C_6$ alkyl, $C_2$~$C_6$ alkenyl, phenyl or benzyl; H on the $C_2$~$C_6$ alkyl is not substituted or substituted by substituent D, $R^2$ is $C_2$~$C_6$ alkyl, and when H on the alkyl is substituted by substituent D, $R^2$ is expressed as $R^D$—$(CH_2)_m$—, m is an integer of 2 to 6, and the substituent D is phenyl, $C_1$~$C_3$ amino, 4-methoxyphenyl and 1,3-dioxolacyl.

3. The method according to claim 1, wherein the catalyst FeX$_2$-8-OIQ complex is a compound shown in Formula IV, wherein $R^{11}$, $R^{12}$, $R^{13}$, $R^{14}$, $R^{15}$, $R^{16}$ and $R^{17}$ are H; $R^{10}$ is $C_1$~$C_4$ alkyl or diphenylmethylene; $R^9$ is $C_1$~$C_4$ alkyl, benzyl, phenyl or 2,6-diisopropylphenyl; $R^{18}$ is selected from the group consisting of $C_1$~$C_4$ alkyl, benzyl or phenyl; X is Cl or Br.

4. The method according to claim 1, wherein the FeX$_2$-8-OIQ complex is shown in Formula IV-1 or Formula IV-2,

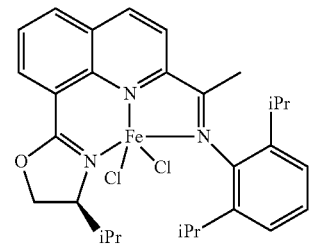

IV-1

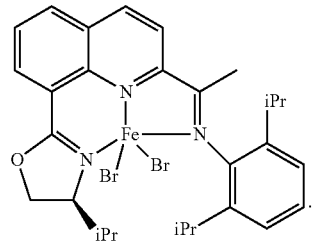

IV-2

5. The method according to claim 1, wherein the silane compound is benzene silane or n-octadecyl silane.

6. The method according to claim 1, wherein an organic solvent is added to the method, and the organic solvent is selected from the group consisting of benzene, carbon tetrachloride, toluene, tetrahydrofuran, ether, dichloromethane, acetonitrile, dioxane, petroleum ether, cyclohexane, n-hexane, ethyl acetate, chloroform, and dimethylformamide.

7. The method according to claim 1, wherein the mole ratio of the disubstituted olefin shown in Formula I, $FeX_2$-8-OIQ complex, silane compound, acetonitrile and reducing agent is 1:0.00001-0.1:0.02-0.2:0.1-0.3:0.06-0.3.

8. The method according to claim 1, wherein the reaction temperature is 0° C.~room temperature.

* * * * *